United States Patent [19]

Manes

[11] Patent Number: 4,548,198
[45] Date of Patent: Oct. 22, 1985

[54] AUTOMATIC TOURNIQUET
[75] Inventor: Michael R. Manes, Littleton, Colo.
[73] Assignee: Aspen Laboratories, Inc., Englewood, Colo.
[21] Appl. No.: 485,546
[22] Filed: Apr. 15, 1983
[51] Int. Cl.[4] ............................................. A61B 17/12
[52] U.S. Cl. .................................................. 128/327
[58] Field of Search ................ 128/327, 682, 683, 686
[56] References Cited
FOREIGN PATENT DOCUMENTS
2085198 4/1982 United Kingdom ................ 128/327

Primary Examiner—Michael H. Thaler

[57] ABSTRACT

A pneumatic tourniquet which automatically adjusts the pressure in the tourniquet cuff and in which the pressure adjustment is variable and depends on the sign and magnitude of the pressure error. There is an inflatable cuff, a motor and pump for inflating the cuff, a valve for deflating the cuff, a transducer for sensing the pressure in the cuff, and a switch for setting a desired cuff pressure. A microprocessor is responsive to signals from the transducer and switches to calculate a duty cycle related to the pressure error. The microprocessor periodically applies a signal to the motor or valve during the calculated duty cycle to provide an adjustment to cuff pressure related to pressure error. The microprocessor also is responsive to motor speed and accumulated error history to provide further adjustments to the pressure.

9 Claims, 11 Drawing Figures

AUTOMATIC TOURNIQUET

BACKGROUND OF THE INVENTION

1. Field of the Invention

The invention in general relates to the field of medical pneumatic tourniquets, and more particularly to a tourniquet which is automatically controlled to maintain the desired tourniquet pressure.

2. Description of the Prior Art

Tourniquets are used in medicine to stop the flow of blood into a patient's limb. A typical use is to provide a "bloodless field" in which surgical procedures may be performed on a limb, without the field being obscured by blood, and without loss of blood to the patient. Tourniquets are also used in emergency procedures to prevent loss of blood when a limb is damaged or in any other instance where it is desired to prevent blood flow to a limb.

Tourniquets conventionally consist of an inflatable cuff which is wrapped around the patient's limb, and a source of compressed gas for inflating the cuff. In order to successfully stop the flow of blood, the pressure in the cuff must be above the highest level of the patient's blood pressure. However, it should not be so high that it damages the tissue of the limb. Thus in conventional tourniquets a pressure gauge for measuring the cuff pressure, and a pressure regulating mechanism is provided.

Up until very recently, conventional pneumatic tourniquets have been manually controlled mechanical devices. That is, a mechanical pressure gauge indicated the pressure visually and the pressure was adjusted by an attendant using a mechanical valve.

Recently, an automatic tourniquet for medical use has been created by Dr. James A. McEwen. This tourniquet is described in U.S. patent application Ser. No. 193,145 filed Oct. 2, 1980. An improved automatic tourniquet is described in U.S. patent application Ser. No. 337,152 filed Jan. 5, 1982, also by Dr. James McEwen. In these automatic tourniquets, the pressure in the cuff is continuously sensed and adjusted by a microprocessor. In addition, the microprocessor activates alarms if a dangerous pressure condition is sensed. It has been found that such automatic tourniquets systems not only are much more convenient in the operating room setting, but also significantly reduce the incidence of limb paralysis, nerve damage and other injuries attributable to tourniquets.

The above-described prior art automatic tourniquets regulate the tourniquet cuff pressure by actuating pressure correcting means if the pressure rises above or falls below a fixed limit. The tourniquets compare the sensed pressure to the desired pressure and if the sensed pressure exceeds a fixed limit, for example 6 mmHg above the selected pressure, then the cuff is deflated a fixed amount, while if the sensed pressure is below the desired pressure by a prescribed limit, the cuff is inflated for a fixed time period, such as two seconds.

The above-described manner of compensating for pressure errors in the prior art system can lead to a cuff pressure which oscillates about the desired pressure.

SUMMARY OF THE INVENTION

It is an object of the present invention to provide a pneumatic tourniquet system in which the pressure adjustment is variable.

It is another object of the invention to provide a pneumatic tourniquet system in which the pressure adjustment depends on the magnitude of the pressure error.

It is a further object of the invention to provide a pneumatic tourniquet system in which the cuff pressure does not oscillate about the desired pressure.

The invention provides an inflatable cuff, a pressure sensing means for producing a first signal representative of the pressure in the cuff, means for producing a second signal representative of a selected pressure, and means responsive to said first and second signals for providing a pressure adjustment to said cuff from a range of pressure adjustments including at least a plurality of possible adjustments for increasing the pressure. Preferably the range also includes at least a plurality of possible adjustments for decreasing the pressure. It is contemplated that the pressure adjustment values may vary continuously over the range or may vary in discrete steps over the range; in the preferred embodiment the pressure adjustment values vary in discrete steps.

In another aspect the invention provides a pneumatic tourniquet comprising an inflatable cuff, a pressure sensing means for producing a first signal representative of the pressure in the cuff, a means for producing a second signal representative of a selected pressure, a means responsive to the first and second signals for determining a pressure adjustment related to the selected pressure and the sensed pressure and for providing a third signal representative of the adjustment, and a means responsive to the third signal for adjusting the pressure in the cuff. Preferably, the means for determining further comprises a means for determining an adjustment dependent on the magnitude of the difference between the selected pressure and the sensed pressure. The means for adjusting may comprise a means for varying the rate of flow of fluid to the cuff in a plurality of graduated steps.

In another aspect the invention comprises an inflatable cuff, a means for selecting a desired cuff pressure, a means for producing a signal representative of the error history of the pressure in the cuff, and a means responsive to the signal for adjusting the pressure in the cuff.

Preferably the means for adjusting in the various aspects of the invention includes a motor and a pump, and the invention further includes a means for producing a signal representative of the speed of the pump or motor, and the means for adjusting the pressure is responsive to this speed signal.

The means for determining a pressure adjustment and providing a signal representative of the adjustment preferably comprises a means for establishing a cycle period and a means for determining a portion of the cycle period related to the difference between the selected pressure and the desired pressure. Preferably the means for adjusting comprises a means for adjusting the rate of fluid flow to or from the cuff by activating a motor or valve for the determined portion of the cycle period. The invention also includes a number of other embodiments which shall be discussed in the detailed description below.

An automatic tourniquet according to the invention smoothly approaches and stays substantially at the selected pressure. Although the oscillations of the prior art tourniquets about the selected pressure were not harmful to the patients, it has been found that a tourniquet which does not present a continuously changing pressure reading provides important psychological advantages. The nurses and physicians who are already under the considerable strain of a surgical procedure, are not put under the further strain of the apparent variation of an important parameter. Further, the steady pressure under standard operating conditions, leads to a faster response of the responsible persons when the pressure begins to vary in an abnormal fashion. Thus, the tourniquet of the present invention has been found to be safer than the prior art tourniquets.

Experience with the tourniquet of the invention has shown it to have a number of other important advantages. The tourniquet is able to hold the desired pressure even in the presence of persistent defects in the tourniquet, such as a steady leak. Thus the invention not only prevents the oscillation of the pressure about the selected pressure, but also provides a stable pressure under a wide variety of operating conditions.

Numerous other aspects, features, objects and advantages of the invention will now become apparent from the following detailed description when read in conjunction with the accompanying drawings, in which:

DESCRIPTION OF THE PREFERRED EMBODIMENT

Figure 1:
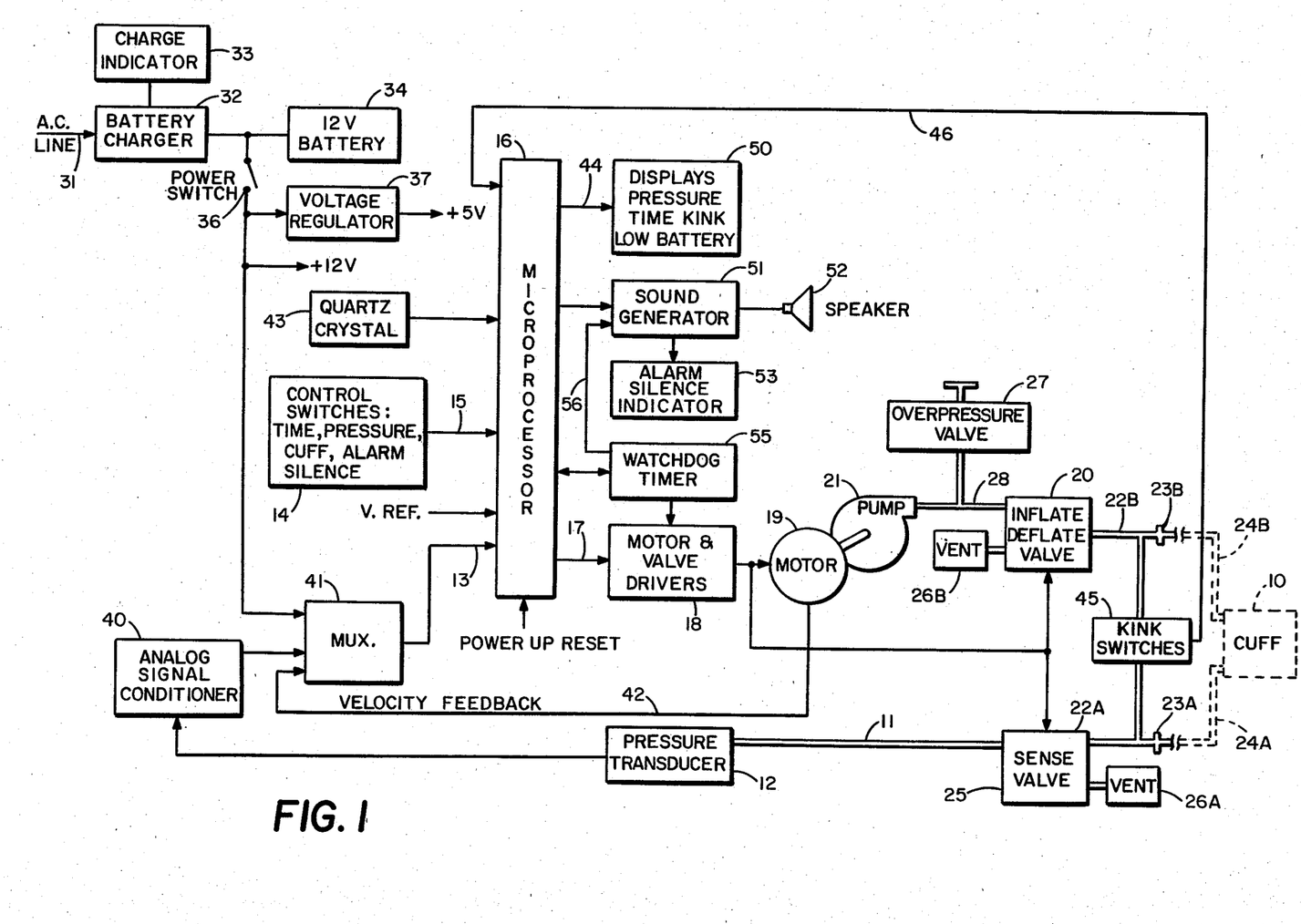
FIG. 1 is block diagrammatic illustration of the invention showing the various functional elements of the preferred embodiment.

Referring to FIG. 1, an automatic pneumatic tourniquet system according to the preferred embodiment of the invention is shown. An inflatable cuff 10 is connected via pressure line 11 to a pressure transducer 12. The cuff 10 is shown in dotted line because it is separable from the automatic tourniquet system, and may be purchased separately. A signal representating the pressure measured by pressure transducer 12 is applied via electrical line 13 to microprocessor 16. One of the control switches 14 is used to apply a signal on line 15 to microprocessor 16 to set a selected pressure. Microprocessor 16 is programmed to calculate a cuff pressure adjustment related to the sensed pressure and the selected pressure, and produces an output signal on line 17 which indicates the cuff pressure adjustment. Electronic motor and valve drive circuitry 18 is responsive to the signal on line 17 to produce a drive signal which is applied to motor 19 and inflate-deflate valve 20. The motor 19 drives a pump 21 at a rate determined by microprocessor 16 to inflate cuff 10 through line 24B. Valve 20 vents the pressure in cuff 10 via vent 26B at a rate determined by microprocessor 16.

Turning now to a more complete description of the preferred embodiment of the invention, power is applied to the tourniquet through AC line 31 or via 12-volt battery 34. A battery charger 32 maintains battery 34 in a charged condition while the AC power is available. A charge indicator 33 indicates that battery 34 is being charged. Power is applied to the tourniquet systems through switch 36. A voltage regulator 37 provides a five-volt regulated voltage which is used to power the portions of the digital circuit requiring a positive five-volt voltage. A 12-volt voltage output is also provided for portions of the circuitry such as the valves, pumps, and pressure transducer which require a 12-volt power source.

Transducer 12, Analog Signal Conditioner 40, and multiplexer 41 comprise a means for producing a first signal representative of the pressure in the cuff 10. The signal from pressure transducer 12 is applied to analog signal conditioner 40, which adjusts the transducer's signal level in relation to a reference voltage in a manner that enables it to be used more efficiently by the microprocessor. The signal from the analog signal conditioner is applied to an analog multiplexer which gates the signal into the microprocessor at the proper time in which the microprocessor will recognize it. A sample of the motor voltage is also applied to the multiplexer via line 42 and gated into the microprocessor via line 13 at the appropriate time. The timing for the microprocessor 16 is provided by quartz crystal 43. Differential pressure switches 45 are connected between lines 22A and 22B. If any obstruction occurs between lines 22A and 22B, switches 45 apply a signal to microprocessor 16 through line 46.

The microprocessor 16, which is a means for determining a pressure adjustment, utilizes the information and the signals applied to it to control the tourniquet and to provide information to the operator. The motor and valve driver circuitry 18, motor 19, pump 21, and valve 20 comprise a means responsive to the signals from the microprocessor for adjusting the pressure in the cuff, as described above. Signals are also applied from microprocessor 16 to the displays 50 to indicate the selected and sensed pressure, the time the tourniquet has been on, the selected alarm time setting, whether there is an obstruction (kink), and the condition of the battery 34. Signals are also applied to sound generator 51, which intrepets the signals to generate a predetermined sound at speaker 52 indicative of the particular alarm condition. The alarm may be silenced if desired via one of control switches 14, in which case a signal is passed via microprocessor 16 and sound generator 51 to alarm silence indicator 53 to indicate that the alarm has been silenced. Timing signals are passed between microprocessor 16 and a watchdog timer 55, which permits the watchdog timer to detect any timing errors which would indicate malfunction of the microprocessor 16. If a timing error is observed, watchdog timer 55 applies a signal to motor and valve drivers circuitry 18 which shuts off the motor 19 and closes the valve 20 thereby isolating the cuff from the pressurizing and depressurizing mechanism, and via line 56 causes an audible alarm to be sounded.

Sense valve 25 is connected between cuff 10 and pressure transducer 12. The sense valve 25 connects the pressure transducer 12 to atmosphere through vent 26A during the tourniquet's start-up sequence in order to correct the pressure transducer's zero offset. Overpressure valve 27 is connected to the line 28 between pump 21 and inflate-deflate valve 20. This is a manually adjustable valve which limits the maximum pressure delivered to the cuff in the event that all other safeguards in the motor/pump control system fail.

Figure 2A:
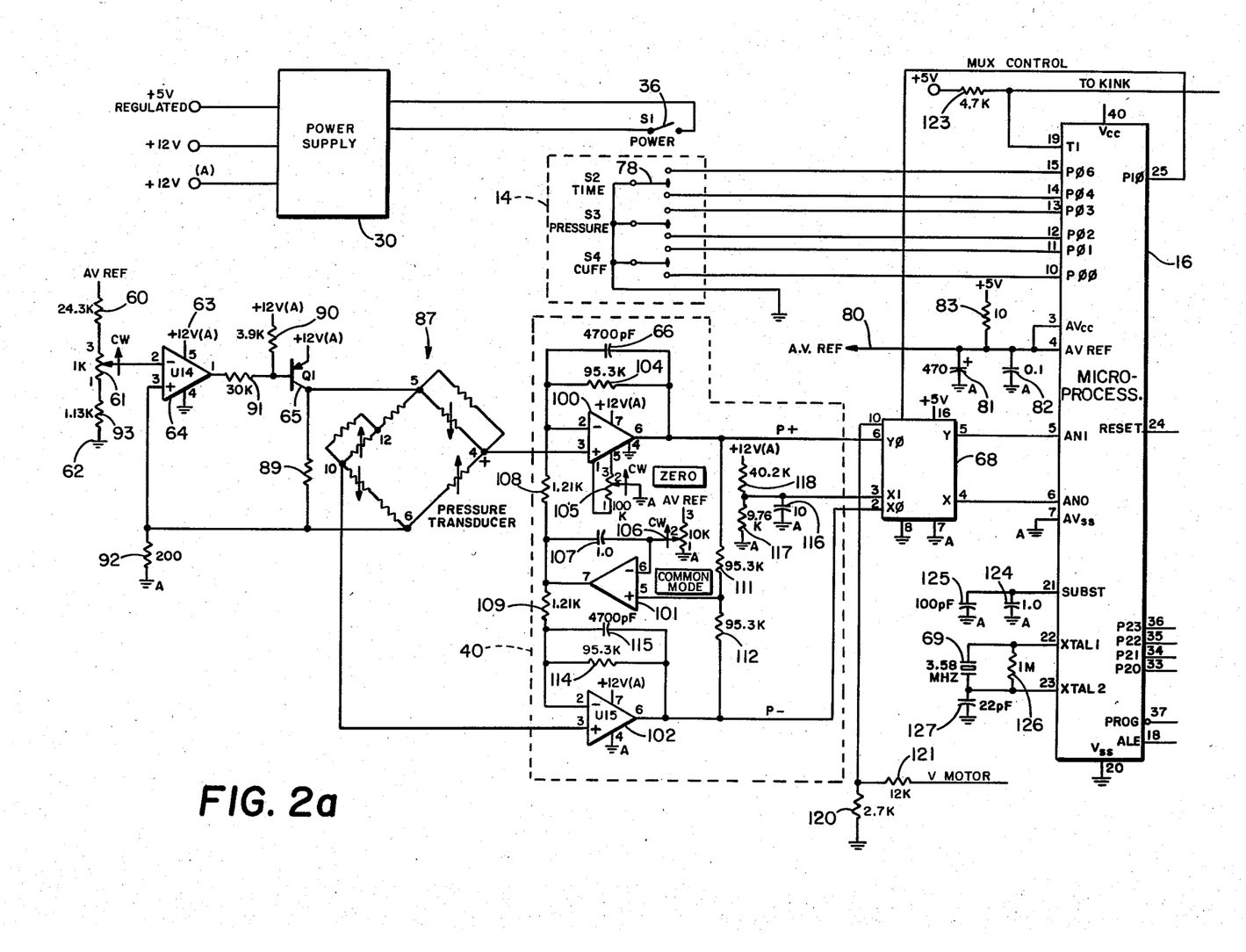
FIG. 2a is the left half and FIG. 2b is the right half of a diagram showing the electronic circuitry in the preferred embodiment of the invention.
Figure 2B:
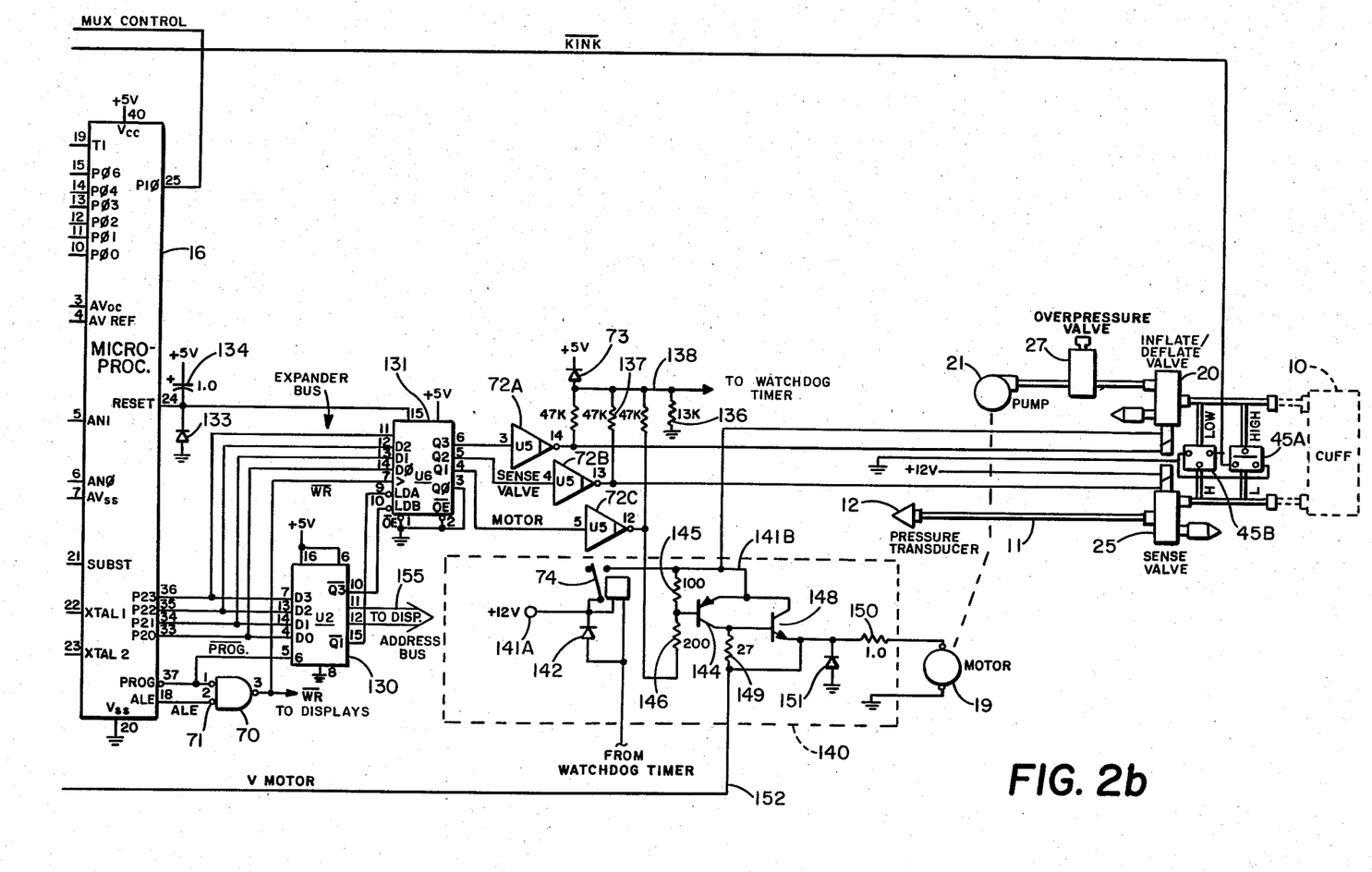

The detailed electronic circuitry of the invention is shown in FIGS. 2a and 2b. These figures do not include all the electronic circuitry of the tourniquet shown in FIG. 1, but only those portions which are relevant to the invention claimed herein. Microprocessor 16 is shown at the right of FIG. 2a and at the left of FIG. 2b in order to provide continuity between the two Figs. If the two Figs. are placed with the microprocessor 16 in each of the Figs. superimposed, the connections between the circuits of the two Figs. will be evident.

The electrical components in FIGS. 2a and 2b are shown by their common electrical symbols, when such symbols exist. Reviewing these symbols, starting from the left in FIG. 2a and proceeding to the right in FIG. 2b, resistors are shown as at 60, with a notation next to the resistor indicating the value of the resistor, as for example, resistor 60 has the resistance 24.3 kilo-ohms. 61 is a potentiometer for which the tap moves as indicated by the arrow when turned clockwise. A ground is shown at 62. Both an analog and a digital ground are provided, with the analog ground being shown by (A) next to the ground. A voltage input is shown by an indicated voltage at the end of a line such as at 63. As will be discussed below, four input voltages are available in the circuit: positive 12-volts digital indicated by a +12 V, positive 12 volts analog indicated by a +12 V(A), positive 5-volts regulated indicated by a +5 V, and a stable positive 5-volt reference voltage indicated by AVREF. An operational amplifier is shown at 64, with the inverted input indicated by the minus sign and the non-inverted input shown by the plus sign. The numbers located at the point of juncture of lines with the electrical components, such as the numbers 2 and 3 located at the connections to the inverting and non-inverting inputs to operational amplifier 64, indicate the pin numbers of the component to which the line is attached. The component indicated at 65 is a transistor. A capacitor is indicated at 66. Each capacitor has its capacitance value indicated next to it. A rectangle, such as 68, is indicitive of an integrated circuit; the particular circuits will be discussed below. At 69 a piezoelectric crystal is shown. Turning to FIG. 2b a negative input NAND gate is shown at 70. The small circles such as 71 at an input or output of a device indicates that that input or output is an inverting input or output. Triangles having a single input and an inverting output, such as at 72 are inverters. A diode is shown at 73, and a relay is shown at 74. The symbols written within the integrated circuits, such as 68, at the point where lines enter or leave the circuit, refer to the signals which are input or output to the circuit at those points. For example, the signal input into microprocessor 16 at line 5 is referred to as the AN1 signal. These signals shall be useful in discussions below regarding the operation of the integrated circuits.

Power to the tourniquet system is supplied by power supply 30, which produces a 5-volt regulated output, and 12-volt outputs for the analog and digital portions of the circuitry. Power is applied to all three outputs when switch 36, located on the front panel of the tourniquet, is closed. Control switches 14, also located on the front panel of the tourniquet, include three single-pole, double-throw, center-off switches such as 78. Switch 52 at 78 controls the length of time that the tourniquet may be left on before an alarm is sounded. In the upward position the switch grounds input 15 to the microprocssor to produce an increase in time setting, while in the lower position switch 52 grounds pin 14 of the microprocessor to produce a decrease in the time setting. Similiarly switch S3 may be used to increase or decrease a selected pressure level, and switch S4 may be used to inflate or deflate the cuff.

A fourth output voltage AVREF is produced at 80. This is an approximately 5-volt output voltage which is isolated from the 5-volt regulated voltage by capacitors 81 and 82 and resistor 83. This reference voltage is applied to pins 3 and 4 of the microprocessor and also to other portions of the circuitry as will be indicated.

The circuitry in the lower left hand portion of FIG. 2a from resistors 60, 61, and 62 through 2 to 1 multiplexer 68 is the circuitry for detecting the cuff pressure and inputing it into the microprocessor. The pressure in the cuff is detected by pressure transducer 87. The pin 5 of transducer 87 is connected to the collector of transistor 65, while pin 6 of the transducer is connected to the collector through resistor 89. The emitter of transistor 65 is connected to the 12-volt analog power supply. The base of transistor 65 is connected to the 12-volt analog power supply through resistor 90 and to the output of operational amplifier 64 through resistor 91. The non-inverting input of operational amplifier 64 is connected to pin 6 of the pressure transducer 87 and to ground through resistor 92. The inverting input to operational amplifier 64 is connected to the output of potentiometer 61. One side of potentiometer 61 is connected to the AVREF voltage through resistor 60, while the other side is connected to the analog ground through resistor 93.

The circuitry 40 between transducer 87 and multiplexer 68 is the signal conditioner circuitry which adjusts the level of the signals from transducer 87. The positively varying (plus) output of transducer 87 (pin number 4) is applied to the non-inverting input of operational amplifier 100. The negatively varying output of transducer 87 (pin 10) is applied to the non-inverting input of operational amplifier 102. Capacitor 66 and resistor 104 are connected in parallel across the inverting input and the output of operational amplifier 100. Potentiometer 105 is connected across the number 1 and number 5 pins of operational amplifier 100. Potentiometer 106 is connected across the AVREF voltage and the analog ground and its output is applied to the inverting input of operational amplifier 101 and to the inverting inputs of operational amplifiers 100 and 102 through capacitor 107 and resistors 108 and 109 respectively. The output of operational amplifier 101 is also connected to the inverting inputs of operational amplifiers 100 and 102 through resistors 108 and 109 respectively. The non-inverting input of operational amplifier 101 is connected to the outputs of operational amplifiers 100 and 102 through resistors 111 and 112 respectively. Resistor 114 and capacitor 115 are connected in parallel across the inverting input and the output of operational amplifier 102. The output of operational amplifier 100 is labeled P+ and is applied to the number 6 pin of multiplexer 68, while the output of operational amplifier 102 is designated P− and is connected to the number 2 pin of the multiplexer. Capacitor 116 and resistor 117 are connected in parallel between the analog ground and the number 3 pin of multiplexer 68. The number 3 pin of multiplexer 68 is also connected to the 12-volt analog power supply through resistor 118. The number 7 pin of the multiplexer is connected to the analog ground while the number 8 pin is connected to the digital ground. The 5-volt regulated power supply is connected to pin 16 of the multiplexer 68. Pin 10 of the multiplexer 68 is connected to ground through resistor 120 and also to the motor circuitry through resistor 121, which connection shall be discussed in reference to FIG. 2b. The control of the multiplexer 68 is provided via connection of pin 9 of the multiplexer to output pin 25 of microprocessor 16. The number 5 output of multiplexer 68 is connected to the number 5 input of microprocessor 16, while the number 4 output of multiplexer 68 is connected to the number 6 input of multiplexer 16. The number 19 input of microprocessor 16 is connected to the kink switches 45A and 45B (FIG. 2b) and also to the 5-volt power supply thru resistor 123. Capacitors 124 and 125 are connected in parallel between the analog ground and pin 21 of the microprocessor. Piezoelectric crystal 69 and resistor 126 are connected in parallel across the number 22 and number 23 input pins of microprocessor 16. Input 23 is also connected to the digital ground through capacitor 127. Pin 20 of the microprocessor is connected to the digital ground while pin 40 is connected to the 5-volt regulated power supply.

Turning now to FIG. 2b, the number 18 output of microprocessor 16 is applied to the number 2 inverted input of NAND gate 70, and pin 37 is inverted and applied to both the inverted input number 1 of NAND gate 70 and to the number 5 pin of quadlatch 130. The output of NAND gate 70 is applied to the number 7 input of four bit register 131 and to the display circuitry 50 (FIG. 1), but this connection shall not be discussed in detail since it is conventional. The microprocessor output pins number 33, 34, 35, and 36 are connected to both the number 4, 14, 13, and 7 input pins respectively of latch 130 and to the number 14, 13, 12, and 11 inputs respectively of four bit register 131. The number 6 and 16 pins of latch 130 are connected to the 5-volt regulated power supply while the number 8 pin is connected to the digital ground. The number 15 and number 10 outputs of latch 130 are connected to the inverted number 9 and number 10 inputs respectively of register 131. The number 1, 2, and 11 pins of latch 130 are connected to the display via address bus 155. The details of this connection shall not be discussed since they are conventional. The inverted number 1 and number 2 pins of register 131 and the number 8 pin are all connected to the digital ground. The number 15 pin of register 131 is connected to the number 24 pin of microprocessor 16, to the cathode of diode 133 and to the 5-volt power supply through capacitor 134. The anode of diode 133 is connected to the digital ground. The number 4, 5, and 6 output pins of register 131 are connected to the inputs of inverters 72c, 72b, and 72a respectively. These three inverters are actually part of a larger Darlington transistor arrary and the inputs of the inverters 72a, 72b, and 72c are the number 3, 4, and 5 pins respectively of the array. Each of the outputs of the inverters 72a, 72b, 72c are connected to the 5-volt digital power supply through a resistor such as 137 and diode 73. The line 138 between the resistors, such as 137, and the anode of diode 73 is connected to the digital ground through resistor 136 and also is provided as an input to the watchdog timer circuitry, which is the subject of a companion application to the present application, and thus will not be described in detail herein. The output of inverter 72a is also applied to inlate/deflate valve 20. The output of inverter 72b is applied to the sense valve 25, and the output of inverter 72c is applied to the motor 19 through the motor circuitry 140. The power to the motor circuitry is provided by the 12-volt power supply at 141A. One of the control terminals of the relay is attached to the 12-volt power supply 141A and the other is attached to a line from the watchdog timer circuitry. These terminals are also connected through diode 142 with the cathode of the diode being toward the power supply. The relay input line is connected to the 12-volt power supply and the output line 141B is connected to the inflate/deflate valve, to the emitter of transistor 144, and the base of transistor 144 through resistor 145. The base of transistor 144 is also connected to the output of inverter 72c through resistor 146. The collector of transistor 148 is connected to the emitter of transistor 144 and to the relay output line 141B. The base of transistor 148 is connected to the collector of transistor 144 and also to its own emitter through resistor 149. The emitter of transistor 148 is also connected to the input to motor 19 through resistor 150 and to the cathode of diode 151. The motor 19 is also connected thru resistor 150 to line 152 which provides a sample of the motor voltage as an input to microprocessor 16 (see FIG. 2a). The other side of the motor 19 is grounded. Valve 25 is also connected to a 12-volt power supply. One terminal of kink switches 45A and 45B is grounded, while the other terminal is applied to the microprocessor as discussed in reference to FIG. 2a. The mechanical connection of motor 19 to pump 21 is shown by a dotted line.

The various electronic components may be purchased at an electronic supply house. Operational amplifiers 64 and 101 are together an LM358 dual op-amp. Amplifiers 100 and 102 are CA3160 op-amps. Transistors 65 and 144 are MPS6533's. Transducer 87 is a Foxboro series 1800 transducer. Multiplexer 68 is a Motorola MC14551. Crystal 127 is preferably a 3.58 MHZ crystal. Microprocessor 16 is preferably an Intel 8022 single component 8-bit microcomputer with on-chip A/D converter. Negative input NAND gate 70 is actually purchased as a CMOS Quad OR gate, type 4071. Diodes 133 and 73 are preferably 1N4148 diodes. Latch 130 is preferably a 4042, while register 131 is preferably a type 4076. As mentioned above 72a, 72b, and 72c are part of a Darlington transistor array ULN2003. Diodes 142 and 151 are preferably 1N4004 diodes. Transistor 148 is preferably a MJE3055T. The other components such as the resistors, capacitors, and relay are all standard. There are, of course, many equivalent electronic components that can replace the components described above.

Valves 20 and 25 are Clippard Model EV0-3-12 valves and may be obtained from Clippard Instrument Laboratories, Inc. 7390 Colerain Road, Cincinnati, Ohio. Valve 27 is preferably a Clippard CS-30-393 regulator. The muffled vents 26A and 26B are Clippard model 1507 mufflers. Motor 19 is a 12-volt DC motor. Any suitable pump 21 may be used, although the preferred embodiment is disclosed in a companion application to the present application. Kink switches 45A and 45B are preferably Fairchild PSF100A-20C differential pressure switches available from Fairchild/Schlumberger, 75 Mall Drive, Commack, N.Y. 11725. The tourniquet cuffs are Inflato-Matic pneumatic tourniquet cuffs which are available from Zimmer, Inc., Warsaw, Ind. 46580. All of the above components are disclosed only as exemplary embodiments of the components of the invention, and many equivalent components may be substituted for them.

A specification and description is available with the Intel 8022 Microprocessor, and any other microproccessor that can be substituted in the invention.

Using this description, and the knowledge generally available with respect to the programming of such microprocessors, suitable programs for carrying out the invention can be constructed from the materials disclosed herein. Many such programs are possible. We shall discuss below the preferred embodiment of such a program that has been implemented to carry out the invention.

Figure 3A:
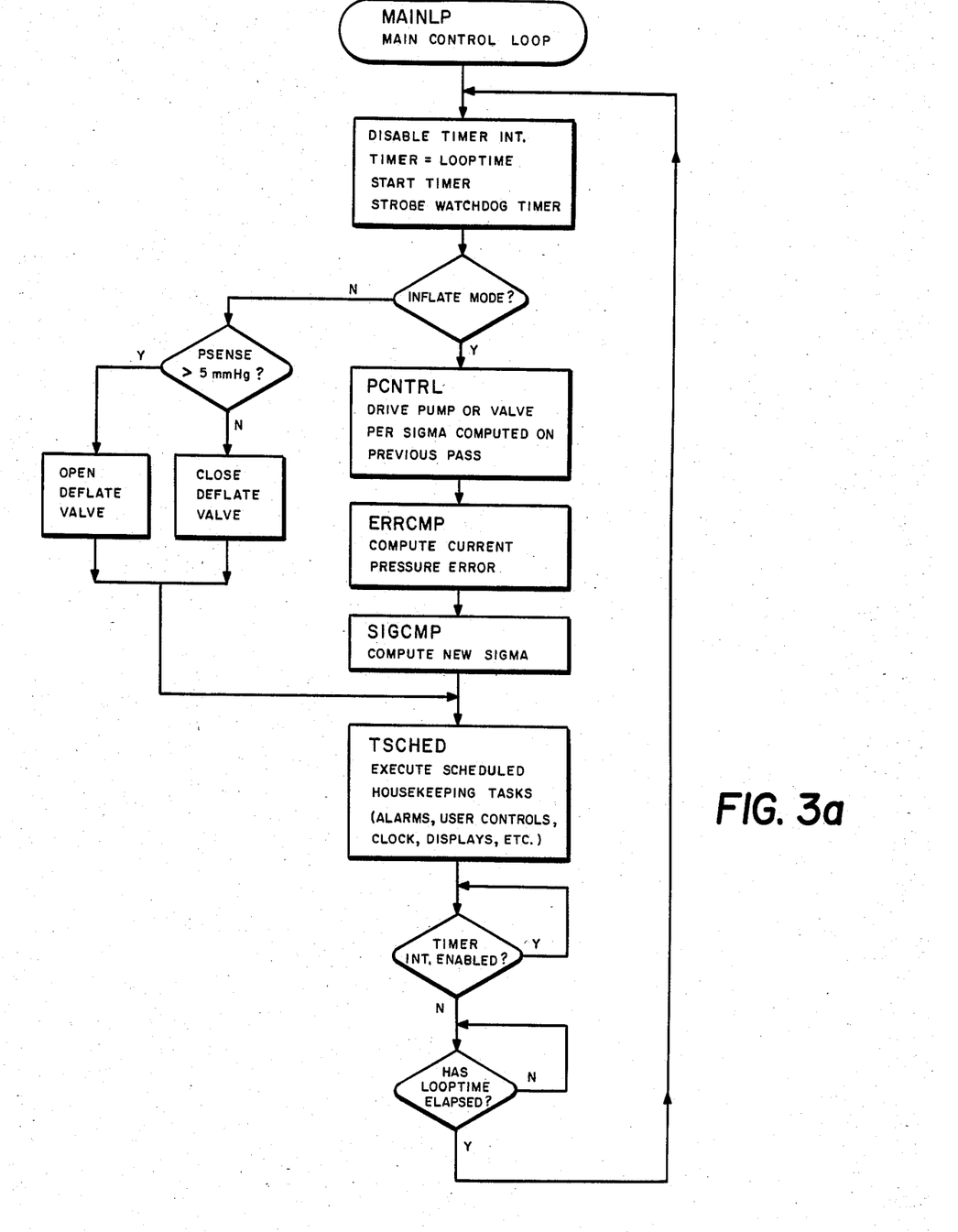
FIGS. 3a through 3f are flow-charts showing a preferred embodiment of the sequence of operations within the microprocessor according to the invention.

The main microprocessor program loop is shown in FIG. 3a. This program controls the timing of the running of the motor 19 and the opening and closing of valve 20 to control the pressure in cuff 10. The timing of the main loop is controlled by an internal microprocessor timer which causes the loop to repeat with a period $T_L$, of 34 milliseconds as shall be described below. Within the loop, a time $T_{pw}$ is calculated, which is the pulse width time, i.e. the time over which the motor may be on or the valve 20 may be open. On the next loop after which $T_{pw}$ value is calculated, the pump 21 or valve 20 may be energized from the time $T_0$ to $T_{pw}$. At the time $T_{pw}$ the internal microprocessor timer generates an interrupt to the microprocessor control, and the same timer is loaded to finish the loop, i.e. to continue for the time ($T_L$-$T_{pw}$).

Turning now to a more detailed description of the program, in reference to FIGS. 1, 2a, 2b, and FIG. 3a, the program first resets both the internal microprocessor timer and the watchdog timer. The watchdog timer is set by a strobe signal from the microprocessor which is produced by a sub-program WDTSTB. If the operator has indicated that the cuff is to be deflated, the internal timer is set to $T_L$ and, if the sensed cuff pressure exceeds 5 mmHg, the deflate valve is opened. If the operator has indicated that the cuff should be inflated, the program control passes to the PCNTRL program (see FIG. 3b). The PCNTRL program first sets the intermediate valuable ONTIME to a low nominal value. It then checks the T1 signal (microprocessor input line 19) to determine if there is a blockage in the tourniquet fluid system. If there is a blockage, the KINK flag is set for subsequent processing in another sub-program, and the value of SIGMA is forced to zero to prevent activities of the pump 21 or valve 20. If there is no blockage, the KINK flag is cleared and the value of SIGMA calculated on the previous loop (see below) is left unaltered. The program then tests for SIGMA equal to zero. If it is, then control bypasses turning the pump 21 or valve 20 on and ONTIME remains at the nominally low value set earlier. If SIGMA is not zero and is negative, then ONTIME is made equal to one-half of the absolute value of SIGMA, and the deflate valve 20 is opened. Otherwise, SIGMA is assumed to be positive and non-zero, indicating the need to supply fluid to the cuff. In this case, ONTIME is made equal to SIGMA, and the pump 21 is turned on.

Figure 3B:
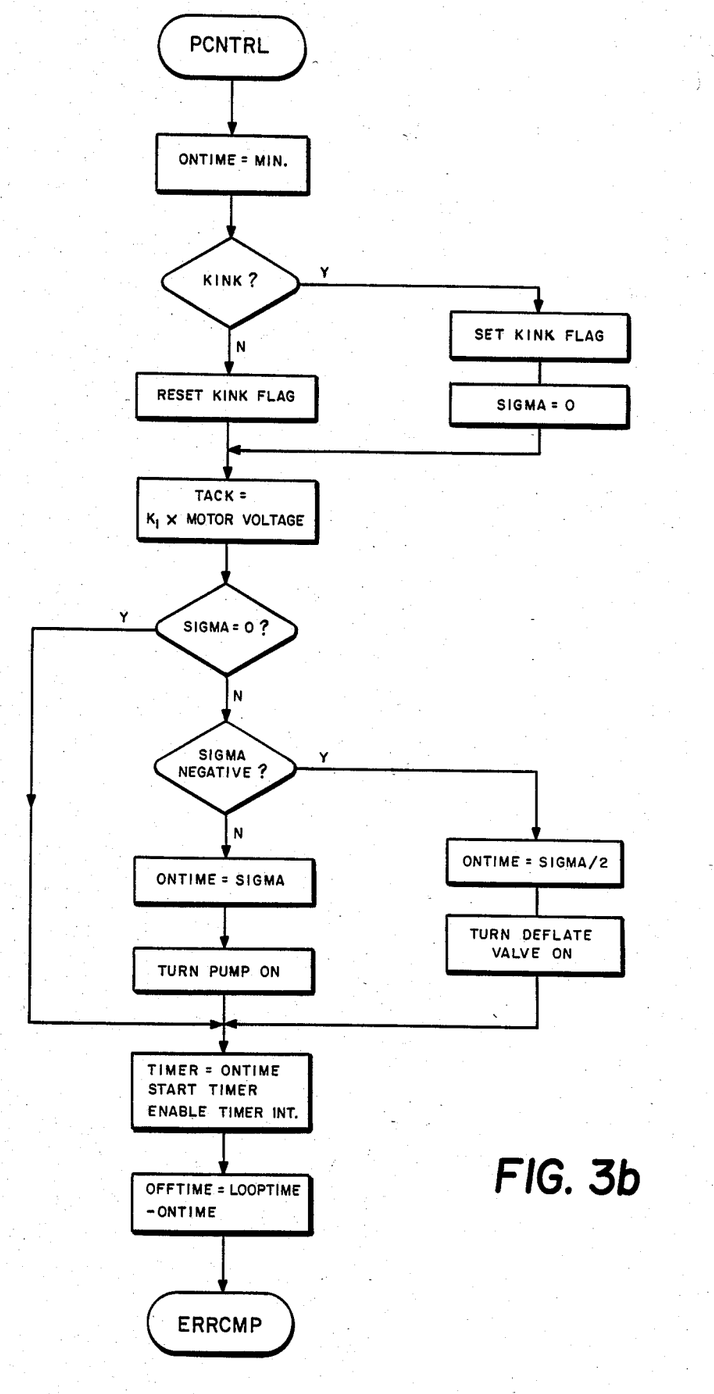

At this point any necessary pump or valve activity has been initiated and ONTIME has been determined. The internal timer is loaded with the value of ONTIME, started, and its interrupt enabled. At the end of the PCNTRL program, program control passes to the ERRCMP program.

Figure 3C:
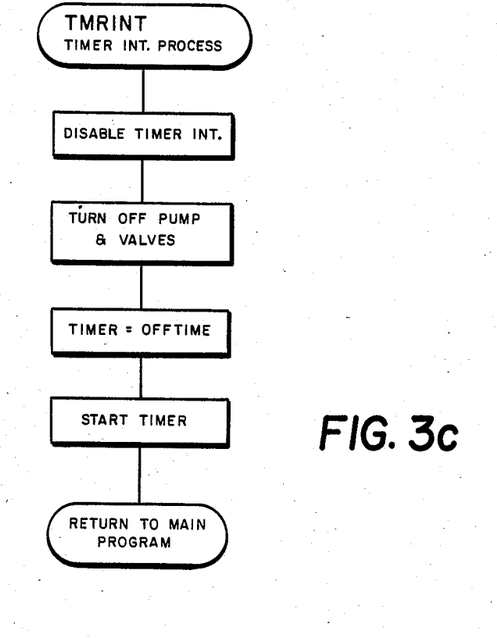

The timer will generate an interrupt when the programmed period has elapsed. This programmed period will be 265 microseconds times the number (ONTIME) the timer is loaded with, since the 8022 microprocessor increments its values every 265 microseconds. This time, $T_{pw}$, will be equal to MIN×265 microseconds=265 microseconds if a kink was detected (see above), SIGMA×265 microseconds if the motor 19 is to be turned on, or −(SIGMA/2)×265 microseconds if the valve 20 is turned on. The calculation of SIGMA will be discussed in detail below. The interrupt causes normal program execution to cease temporarily and the timer interrupt (TMRINT) routine (FIG. 3c) to be executed. This routine will turn off both the motor/pump 19/21 and deflate valve 20, disable the timer interrupt and restart the timer with a value OFFTIME=$T_L$−$T_{pw}$. Control then returns to the point in the main program at which the interrupt occurred.

Figure 3D:
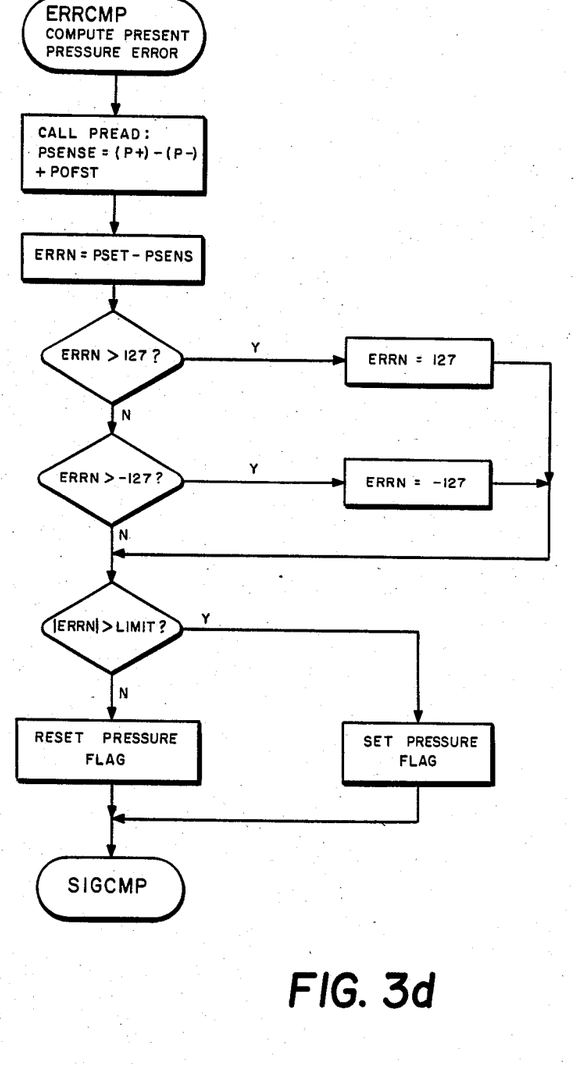
Figure 3E:
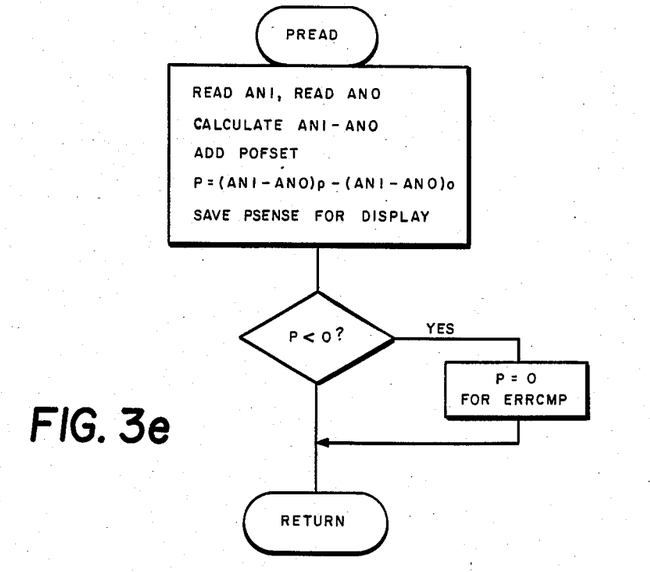

The ERRCMP program is shown in FIG. 3d. This program calculates the pressure errors. The program first obtains the current sensed pressure. This pressure is obtained via the PREAD program, which is shown in FIG. 3e. The PREAD program reads the AN1 and AN0 signals from the 5 and 6 pins of the microprocessor and calculates their difference. This pressure is then corrected by an offset pressure to obtain the sensed pressure, PSENSE. The offset pressure, POFSET, is found in a calibration cycle when the tourniquet is turned on and is equal to the negative value of the apparent pressure, (AN1−AN0) at zero input pressure. This pressure is stored in the microprocessor memory. PREAD then saves the value PSENSE for the display. If the value of PSENSE calculated is less than 0, then PSENSE is set to 0 for the ERRCMP program. The ERRCMP program then calculates ERRN=PSET−PSENSE. The value ERRN is then limited to the range between −127 and +127. If the absolute value of ERRN is greater than a limit, which in the preferred embodiment is 14 mmHg, a pressure alarm flag is set for subsequent processing by the alarm housekeeping routine.

Figure 3F:
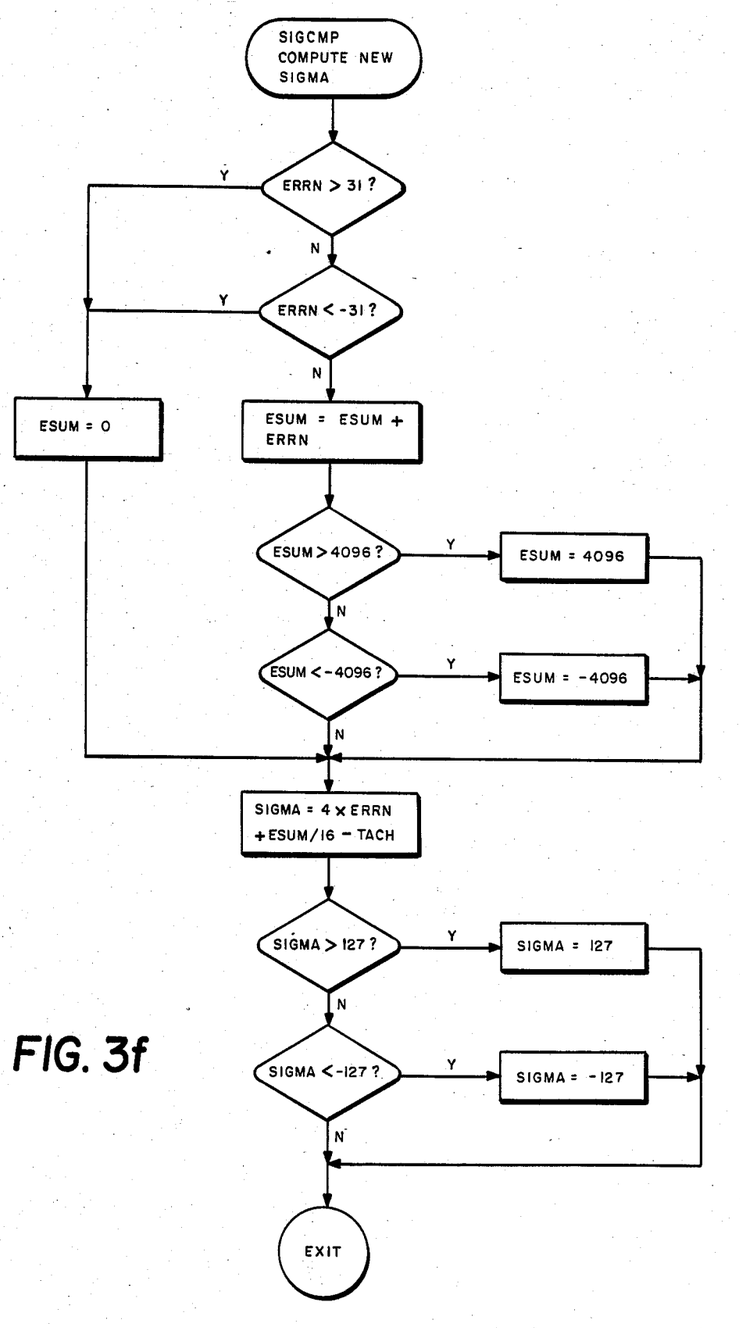

The value of SIGMA is calculated by the SIGCMP sub-program shown in FIG. 3f. According to invention, it is desirable that the on time be related to at least two factors: (1) the history of past pressure errors of the system; (2) the current pressure error of the system. A mathematical equation describing this algorithm is SIGMA=J×ERRN+K×ERRN−TACH. The coefficients J and K may be determined analytically by application of classical control theory, given the frequency response of the function ERRN/SIGMA, or J and K may be determined empirically in operation to obtain a satisfactorily low steady-state and transient error. In the preferred embodiment, J=1/16 and K=4. The invention also provides for adding a third term which is proportional to the pump motor speed. This term may be defined as TACH=N×(motor speed). As indicated above, the motor speed is sensed by sampling the back EMF which the motor produces between drive pulses. The inclusion of this intermediate feedback term forms a minor velocity loop, which minimizes the amount and duration of error caused by transient disturbances. In the embodiment of the invention the coefficient N is determined empirically and hard-wired with a resistor divider 120, 121. Designating the sum over the previous errors as ESUM and the term N×(motor speed) by TACH, the value of SIGMA may be given in the form SIGMA=ESUM/16+(4×ERRN)−TACH.

Turning now to FIG. 3f, the SIGCMP sub-program solves the above equation, applying certain limits to the values of certain variables. First, the value of ERRN is constrained to the range from −127 to +127 mmHg to permit ERRN to be processed as an 8-bit 2's complement variable. Second, if the absolute value of ERRN exceeds 31, the value of ESUM is set to zero, thereby clearing the memory of past errors and establishing a pure proportional control law for errors in excess of 31. This has the beneficial effect of reducing the degree of pressure overshoot when inflating large cuffs to high pressure from an initially deflated condition. Third, the value of ESUM is constrained to the range −4096 to +4096 to prevent overflow errors in subsequent calculations. Fourth, the value of SIGMA is constrained to the range of −127 to +127, the largest values acceptable to the internal timer. The value of Loop Time ($T_L$) is equivalent to a timer value of 128, so SIGMA may produce duty cycles of −127/128 to +127/128, where positive duty cycles are directed to the pump motor and negative values are directed to the deflate valve. The resulting value of SIGMA is then saved in memory for use on the next pass through PCNTRL.

Returning now to FIG. 3a, after the value of SIGMA is calculated the program then turns to housekeeping chores. We shall not detail these housekeeping functions since they do not form a part of the present invention. Upon completion of a scheduled housekeeping routine, the program will execute an idle loop until the balance of $T_L$ has elapsed. This delay is executed by first awaiting the completion of $T_{pw}$, should that time interval not yet be complete as indicated by the timer interrupt enable flag being true. If the interrupt is not enabled, the program will wait until the timer has finished counting OFFTIME, at which time it will start processing another loop as described above.

In order that the interaction of the various parts of the system be more fully understood, a brief description of the operation of the system will now be given. The transistor 65 and amplifier 64 and the associated resistors supply a nominal 1.8 milliamp current to the transducer 80. The gain (span) of the transducer in millivolts per millimeter Hg is adjustable by varying potentiometer 61. With zero gauge pressure applied to the transducer, its output is nominally minus 60 millivolts. The transducer is nulled at a gauge pressure of 247 mmHg. The amplifiers 100 and 102 and the associated circuitry provide a differential amplifier for increasing the signal level of the outputs of the transducer 87. Offset errors contributed by the transducer and the amplifiers are adjusted out with potentiometer 105. The level of the common-mode output voltage of the amplifiers 100 and 102 is set by potentiometer 106.

When the MUC control signal from the microprocessor is low the signal P+ and P− appear on the 5 and 4 output pins respectively of multiplexer 68, and the microprocessor directs thre AN1 and AN0 signals to an A/D converter internal to the microprocessor, which provides the pressure signals PSENSE to the microprocessor at a time determined by the program discussed above. When the MUX control signal is high then multiplexer 68 feeds the scaled motor back EMF on input 10 to its 5 output, and the microprocessor reads AN1 as the motor back EMF. This value is fed into the program as TACH as discussed above. Also as indicated above the selected pressure is set in the microprocessor register through switch S3.

Figure 4A:
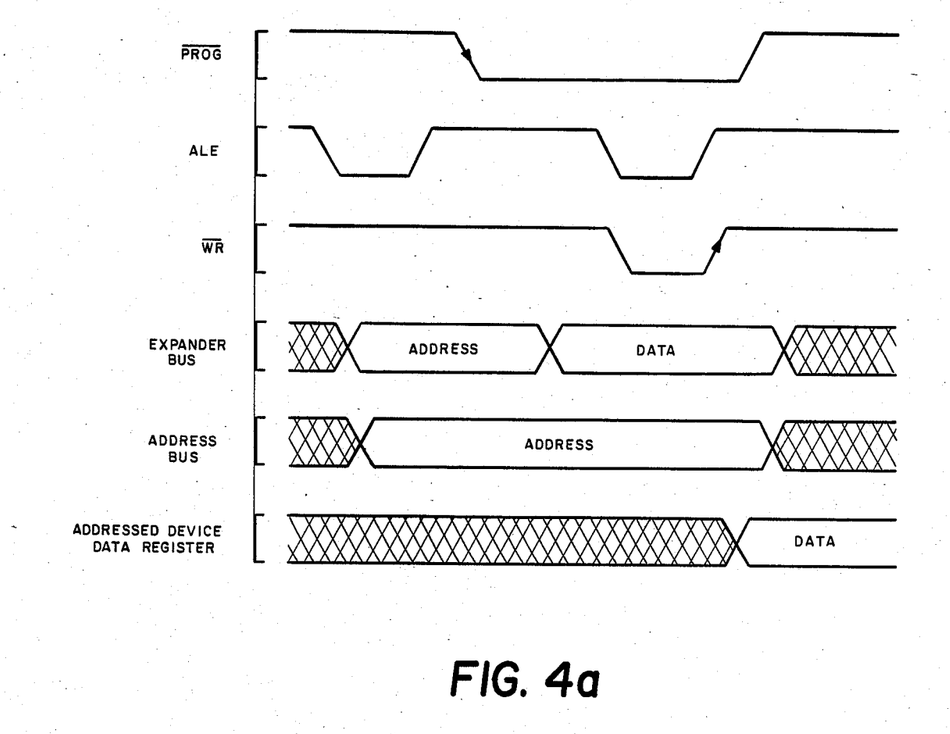
FIGS. 4a and 4b are timing diagrams illustrating the timing of the signals sensed by or developed at various points in the electronic circuitry of FIGS. 2a and 2b during the motor and valve control operations in the preferred embodiment of the invention.

The microprocessor executes control over power to operate the pump motor 19, 21 the sense value 25 and the inflate/deflate valve 20 by means of four output signals, i.e., P20, P21, P22, P23, and the ALE and /PROG timing signals. FIG. 4a illustrates the information contained in and the timing relationship of these signals.

ALE is a free-running 119 kHz signal used to synchronize external events. /PROG is a signal which is in a high voltage (false) state except when certain input/output instructions are executed by the 8022 microprocessor; these instructions are known jointly as expander instructions. P20, 21, 22 and 23 are jointly referred to as the expander bus, the joint value of which may take on a 4-bit binary value which may be expressed in decimal form as any one of the integers from 0 through 15.

Upon execution of an expander instruction, the 8022 will drive the expander bus to a value unique to the instruction during the time that /PROG is false (high voltage). The 8022 will then drive /PROG low (true), storing the data on the expander bus in the address latch 130 where it appears as the address bus. The value on the address bus is used to identify to which of 16 possible destinations the subsequent data will be directed. Addresses 8 through 14 identify each of the seven LED display digits, address 5 is for the LED decimal point and address 7 is for the valve/motor register 131.

After /PROG has gone true, the 8022 will change the value on the expander bus to equal that of a program-controlled variable. This value is the data to be transferred to the device addressed by the address bus. The OR gate 70 generates a pulse /WR; logically, /WR=PROG·/ALE. This pulse, /WR, will change from a low to high rate when the expander bus contains valid data and the address bus contains a valid address; the rising edge of /WR is used to store the data in the appropriate register as directed by the address bus.

The microprocessor signals containing the command information for the motor/pump 19, 21, sense valve 25, and inflate/deflate valve 20 are P20, P21, and P22 signals on pins 33 through 35 respectively. The states of these lines in conjunction with the state of P23 (pin 36) and the timing of PROG (pine 37) and ALE (pin 18) determine actuation signals that appear at the inputs to the open-collector inverters. 72a, 72b, and 72c. As an aid to understanding the operation of latch 130 and register 131, FIG. 2b and FIG. 4b and the following text illustrate the sequence of events associated with causing the motor to turn on.

Figure 4B:
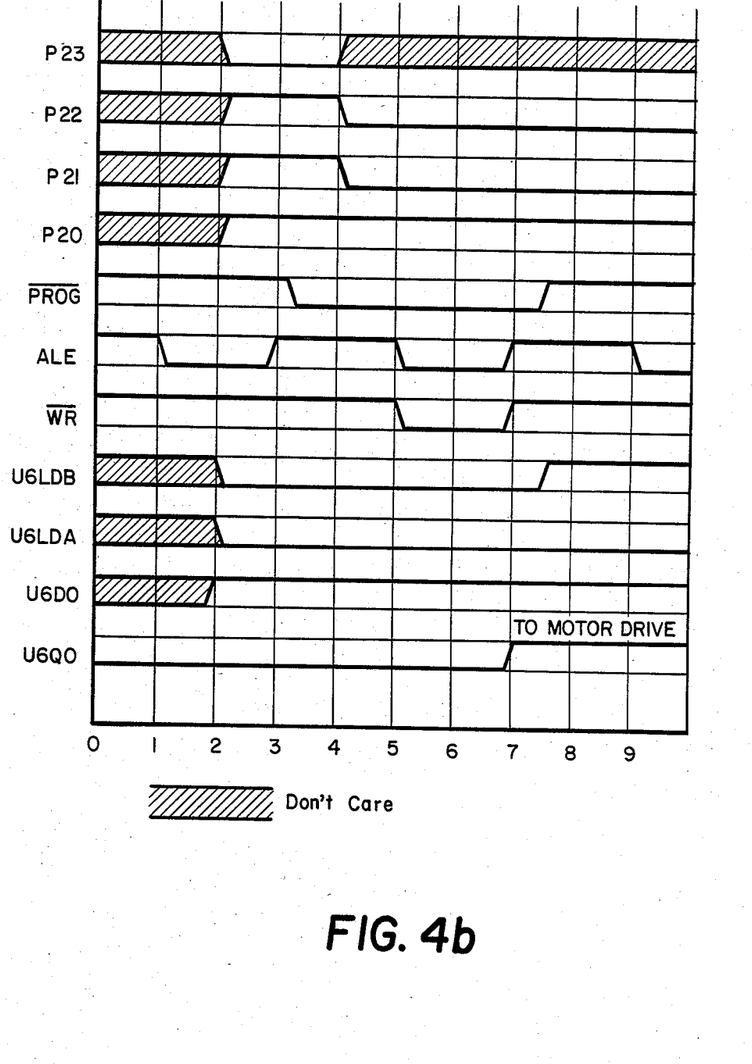

Register 131 is a four-bit, three-state, D register. Its outputs are the command signals to the motor and valves. Data that appears on its inputs, D0 through D3, is gated to its outputs, Q0 through Q3 respectively, and latched when low level signals appear at both load input, pins 9 and 10, and a positive going transition appears at its gate input, pin 7. Note that all outputs are reset to zero when pin 15 is held high. In FIG. 4b the signals of register 131 are given the prefix "U6" to differentiate them from the signals of latch 130.

Latch 130 is a gated, four-bit, D latch. Data that appears on its input terminals, D0 through D3, is gated to its outputs when its gate input, pin 5, is at a high level.

The signals PROG and P20 through P23 are under program control of the microprocessor while ALE is an free-running syncronous timing signal whose frequency is nominally 119 KHz. To initiate the sequence, P20 through P22 are made high while P23 is made low. Note that in this example P20 is the data of interest, P21 is used both as a command to the Sense valve 25 and a load enable for the register 131, P22 is command information to the inflate/deflate valve 20, and P23 is being used as a load enable signal. Since /PROG is high and latch 130 is high-level gated, the states of P21 and P23 will cause the /Q1 and Q3 outputs of latch 130 to go low thus enabling both load inputs of register 131. /PROG is then made low holding the data in latch 30. Next P21 and P22 are caused to go low to keep from energizing the valves. Data is now set up for clocking through register 131. /WR will follow the next positive-going transition of ALE causing the data on the input of register 131 to be latched resulting in a drive command to the motor. The /PROG line then goes high which gates the low P21 signal to the Q1 output of latch 130 causing the LDA input to register 131 to go high disabling the data loads to the register.

The sequence to turn the motor 19 off is similar except that the state of P20 would be inverted. The control of the signal to the inflate/deflate valve 20 is analogous to the motor drive signal while the command to the sense valve 25 is a steady DC signal. When a deflate command is issued to the inflate/deflate valve 20, the command is terminated when cuff pressure is reduced below 5 mmHg to preclude an unnecessarily long term exciation of the valve.

A feature of the invention is that the pump/valve drive waveform generated by the invention is a pulse-width modulated signal for which the average of RMS voltage can be discretely varied over a wide range to control the pump or valve in an amount determined by the pressure control algorithm. Further, full peak voltage is provided on every cycle, which means that the full starting current is provided on each cycle, resulting in high torque at low speeds.

The system according to the invention has been found to operate much more smoothly and quietly than prior art systems. These features are very important in the surgical arena.

The tourniquet according to the invention is also very reliable. The display of the pressure is on a digital LCD which responds to changes as small as 1 mmHg. The prototype system according to the embodiment described above, has held the pressure in a cuff steady, i.e. within 1 mmHg of the desired pressure for several months. As mentioned above, the steadiness of this pressure reading in the operating environment has been found to have important advantages.

A novel pneumatic tourniquet system that provides improved pressure control and stability over a broad range of operating conditions, and has numerous other features and advantages has been described. While the above description of the invention has been referenced to a particular embodiment, it is evident that, now that the advantages of the tourniquet have been disclosed, those skilled in the art can now make numerous uses of, modifications of, and departures from the specific embodiment described herein without departing from the inventive concepts. For example, a wide variety of pumps and motors may be used with the system. The single valve which is controlled to be open for a determined period of time, could be replaced with a series of valves with calibrated orifices, and the algorithm could be programmed to selectively open one or more of the orifices for a fixed period of time. Now that the advantages of the use of the disclosed algorithm for calculating varying pressure adjustments for a tourniquet have been described, it is clear that other terms may be added to the algorithm without departing from the inventive concepts. Similarly, although the invention has been described in terms of the precise electronic parts and the detailed programming that has been used in the prototype embodiment in order to fulfill the requirements of the patent law, a wide variety of different electronics and programming may be used in implementing the invention. Consequently, the invention is to be construed as embracing each and every novel feature and novel combination of features within the appended claims.

What I claim is:

1. A pneumatic tourniquet comprising:
   (a) an inflatable cuff;
   (b) pressure sensing means for producing a first signal representative of the pressure in said cuff;
   (c) means for producing a second signal representative of a selected pressure;
   (d) means responsive to said first and second signals for determining a pressure adjustment related to the selected pressure and the sensed pressure, said means for determining further including a means for varying said pressure adjustment dependent on the magnitude of the difference between said selected pressure and said sensing pressure, and for providing a third signal representative of said pressure adjustment; and
   (e) means responsive to said third signal for adjusting the pressure in said cuff.

2. A pneumatic tourniquet as in claim 1 wherein said means for adjusting comprises means for varying the rate of flow of fluid to said cuff in a plurality of graduated steps.

3. A pneumatic tourniquet as in claim 1 and further including means responsive to said first and second signals for producing a fourth signal representative of the error history of the pressure in said cuff, and said means for determining is further responsive to said fourth signal.

4. A pneumatic tourniquet as in claim 1 wherein said means for adjusting includes a motor and a pump, and further including a means for producing a fifth signal representative of the speed of said motor or pump, and wherein said means for determing is further responsive to said fifth signal.

5. A pneumatic tourniquet as in claim 1 wherein said means for adjusting comprises:
   an electric motor; and
   a pump driven by said motor; and
   wherein said means responsive to said third signal provides an adjustment of the duty cycle of power supplied to said electric motor.

6. A pneumatic tourniquet as in claim 1 wherein said means for determining and providing includes means for establishing a cycle period, and said means for adjusting comprises a pressure release valve and means for opening said valve for a portion of said cycle period.

7. A pneumatic tourniquet as in claim 1 wherein said means for determining and providing comprises:
   means for establishing a cycle period; and
   means for determining a portion of said cycle period related to the difference between said selected pressure and said desired pressure;
   and said means for adjusting comprises means actuated for said portion of said cycle period for adjusting the rate of fluid flow to or from said cuff, so that said rate of fluid flow is related to said difference between said selected and desired pressures.

8. A pneumatic tourniquet as in claim 7 and further including means responsive to said first and second signals for producing a fourth signal representative of the error history of the pressure in said cuff, and said means for determining is further responsive to said fourth signal.

9. A pneumatic tourniquet as in claim 8 wherein said means for adjusting further includes a motor and a pump, and further including means for producing a fifth signal representative of the speed of said motor or pump, and wherein said means for determining is further responsive to said fifth signal.

* * * * *